United States Patent [19]

Trummlitz et al.

[11] 4,233,333
[45] Nov. 11, 1980

[54] 4,5-DIMETHYL-THIENO[3,2-d]ISO-THIAZOLO-3(2H)-ONE-1,1-DIOXIDES, COMPOSITIONS, AND METHODS OF USE AS A SWEETENER

[75] Inventors: Günter Trummlitz; Ernst Seeger; Wolfhard Engel, all of Biberach, Fed. Rep. of Germany

[73] Assignee: Boehringer Ingelheim GmbH, Ingelheim am Rhein, Fed. Rep. of Germany

[21] Appl. No.: 952,958

[22] Filed: Oct. 20, 1978

[30] Foreign Application Priority Data

Nov. 5, 1977 [DE] Fed. Rep. of Germany ....... 2749640
Sep. 9, 1978 [DE] Fed. Rep. of Germany ....... 2839266

[51] Int. Cl.³ .................. A23G 1/236; C07D 275/00
[52] U.S. Cl. ................ 426/548; 260/347.2; 548/210; 549/62
[58] Field of Search ............ 426/548; 548/210; 260/302 A, 302 F

[56] References Cited
FOREIGN PATENT DOCUMENTS 2534689 3/1976 Fed. Rep. of Germany .

OTHER PUBLICATIONS

Lombardino, J. G. J. Org. Chem., vol. 36, No. 13, 1971 pp. 1843-1845.

Primary Examiner—Donald G. Daus
Assistant Examiner—Lisa Jones
Attorney, Agent, or Firm—Hammond & Littell, Weissenberger & Muserlian

[57] ABSTRACT

Compounds of the formula

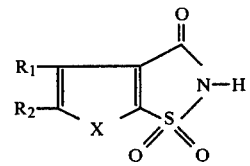

wherein
X is oxygen or sulfur;
$R_1$ is hydrogen, methyl or ethyl; and
$R_2$ is methyl or ethyl;

and non-toxic, physiologically acceptable salts thereof formed with an inorganic or organic base. The compounds as well as their salts are useful as sweetening agents.

3 Claims, No Drawings

4,5-DIMETHYL-THIENO[3,2-d]ISOTHIAZOLO-3(2H)-ONE-1,1-DIOXIDES, COMPOSITIONS, AND METHODS OF USE AS A SWEETENER

This invention relates to novel condensed isothiazolo-3(2H)-one-1,1-dioxides and salts thereof, a method of preparing these compounds, and methods of using them as sweetening agents.

More particularly, the present invention relates to a novel class of compounds represented by the formula

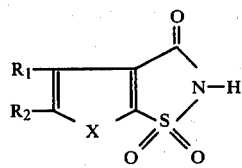

wherein
X is oxygen or sulfur;
$R_1$ is hydrogen, methyl or ethyl; and
$R_2$ is methyl or ethyl;
and non-toxic, physiologically acceptable salts thereof formed with an inorganic or organic base.

BACKGROUND OF THE INVENTION

Recent toxicological investigations have shown that the use of cyclamate and saccharin as sweetening agents at higher dosage levels is not entirely safe. At the present time, however, there is no substitute for these sweetening agents on the market. Also, tests with certain natural substances or dipeptides or oxathiazinone-dioxides have until now failed to provide acceptable successor products which can fully and completely replace the heretofore conventional sugar substitutes with respect to safety, high sweetening power and absence of unpleasant after-taste.

THE PRIOR ART

Thieno[3,2-d]isothiazole-3(2H)-one-1,1-dioxide is disclosed as a sweetening agent in German Offenlegungsschrift No. 2,534,689.

5-Methyl-saccharin is disclosed in J. Org. Chem 36, 1843 (1971).

OBJECTS OF THE INVENTION

It is an object of the present invention to provide novel sweetening agents which are at least equivalent in sweetening power to previously used sugar substitutes and, in addition, are characterized by the absence of unpleasant after-taste and toxic side-effects.

Other objects and advantages of the instant invention will become apparent as the description thereto proceeds.

DESCRIPTION OF THE INVENTION

We have discovered that the above object is achieved by providing the condensed isothiazolo-3(2H)-one-1,1-dioxides of the formula I above and their non-toxic salts formed with inorganic or organic bases.

The compounds embraced by formula I may be prepared by the following method:

A 2-sulfamoyl-3-carboxylic acid derivative of furan or thiophene of the formula

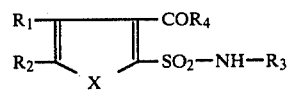

wherein X,
$R_1$ and $R_2$ have the same meanings as in formula I;
$R_3$ is hydrogen or tert. alkyl of 4 to 19 carbon atoms; and
$R_4$ is a nucleophilic exchangeable substituent, such as hydroxyl, alkoxy of 1 to 10 carbon atoms, phenoxy, naphthoxy, halogen, phenyl-(alkoxy of 1 to 3 carbon atoms) or naphthyl-(alkoxy of 1 to 3 carbon atoms);

is treated at temperatures between 0° and 100° C., preferably at 50° to 70° C., with an acid, such as phosphoric acid, polyphosphoric acid, sulfuric acid or a mixture of any two or more of these, whereby a cyclization occurs. The end product is isolated in conventional manner, for instance, by addition of ice to the reaction mixture and purification of the precipitate formed thereby.

The cyclization may, however, also be effected in the absence of a mineral acid by simple heating to temperatures between 100° and 250° C., for instance also in the presence of a solvent such as o-dichloro-benzene or toluene. Also basic reaction conditions, for example reaction in the presence of sodium methylate, have proved to be equally suitable.

The starting compounds of the formula II can, for example, be obtained as follows: From the correspondingly substituted thiophene or furan the corresponding sulfochloride is prepared with chlorosulfonic acid and phosphorus pentachloride. The sulfochloride is then reacted with an amine of the formula $H_2N—R_3$, where $R_3$ has the meanings previously defined, to form a sulfonamide of the formula

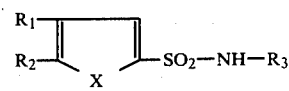

wherein $R_1$, $R_2$, $R_3$ and X have the meanings previously defined. The sulfonamide is thereupon treated, for instance in dry tetrahydrofuran or an analogous ether as a solvent medium, with a lithium alkyl such as n-butyl lithium, which is dissolved in a hydrocarbon such as hexane, at temperatures of about $-40°$ C., and subsequently reacted with carbon dioxide at $-60°$ C. After acidifying the reaction mixture with hydrochloric acid, the reaction product, i.e. the corresponding 2-sulfamoyl-3-carboxylic acid derivative of the formula II is liberated and in conventional manner isolated and purified. For example, we have found that the starting compound of the formula II wherein $R_1$ is hydrogen, $R_2$ is methyl, $R_3$ is tert. alkyl and X is sulfur can be obtained in this manner with a total yield of 60 to 70% of theory from 2-methyl-thiophene.

The condensed isothiazolo-3(2H)-one-1,1-dioxides of the formula I are acid compounds and form salts with inorganic or organic bases. Examples of non-toxic, physiologically acceptable salts are those formed with an alkali metal hydroxide such as sodium hydroxide or potassium hydroxide, an alkaline earth metal hydroxide such as calcium hydroxide, or ammonium hydroxide.

The following examples illustrate the present invention and will enable others skilled in the art to understand it more completely. It should be understood, however, that the invention is not limited solely to the particular examples given below.

EXAMPLE 1

5-Methyl-furo[3,2-d]isothiazole-3(2H)-one-1,1-dioxide

A mixture consisting of 20.5 gm (0.1 mol) of 5-methyl-2-sulfamoyl-furan-3-carboxylic acid, 20.8 gm (0.1 mol) of phosphorus pentachloride and 50 ml of anhydrous toluene was refluxed for eight hours. Thereafter, the hot reaction mixture was filtered, and upon cooling of the filtrate 11.8 gm (62.5% of theory) of 5-methyl-furo[3,2-d]isothiazole-3(2H)-one-1,1-dioxide of the formula

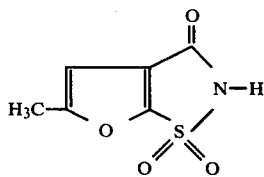

crystallized out. The product was recrystallized twice from benzene, yielding 6.9 gm (37% of theory) of the purified product having a melting point of 195°–196° C. (decomp.).

Analysis:
IR (KBr): 1730 and 1690 cm$^{-1}$ (CO);
$^1$H-NMR (CDCl$_3$+CD$_3$OD): $\delta=6.5$ (s, 1, 4-H), 2.5 (s, 3, CH$_3$) and 1 exchangeable proton:
MS: M$^+$ 187 m/e.
C$_6$H$_5$NO$_4$S (187.18)—Calc.; C-38.50%; H-2.69%; N-7.48%; S-17.13%; Found: C-38.80%; H-2.75%; N-7.46%; S-17.35%.

The starting compound was obtained in the following way: 1 liter of ethylene chloride was admixed with 260 gm (3.17 mol) of 2-methyl-furan and 507 gm (3.17 mol) of sulfur trioxide-pyridine complex, and the mixture was stirred for 3 days. The reaction mixture was then admixed with 3 liters of warm water while stirring, and the aqueous phase was separated and, by means of sodium carbonate, adjusted to a pH-value of 7.5 and then evaporated to dryness. The residue was extracted several times with isopropanol by refluxing, and from the combined and cooled isopropanol fractions 248 gm (43% of theory) of crystalline sodium 5-methyl-furan-2-sulfonate was obtained.

At a temperature of 30° to 50° C., 248 gm (1.35 mol) of sodium 5-methyl-furan-2-sulfonate were admixed in portions with 281 gm (1.35 mol) of phosphorus pentachloride and the mixture was stirred for 15 minutes at 50° C. The reaction mixture was then poured over ice and extracted with ether. The ether phase was washed until neutral, dried and evaporated. The residue (200 gm of 5-methyl-furan-2-sulfonic acid chloride) was dissolved in 500 ml of ether, and the solution was added dropwise to a solution of 280 ml (2.7 mol) of tert.-butylamine in 500 ml of ether at a temperature of 5° to 10° C. After stirring at room temperature and at reflux temperature, each for 2 hours, the reaction mixture was washed with ice water, dilute hydrochloric acid and water and then evaporated. The residue was recrystallized from cyclohexane, yielding 180.5 gm (61.5% of theory) of N-tert. butyl-5-methyl-furan-2-sulfonamide. M.p. 113°–114° C.

$^1$H-NMR (CDCl$_3$): $\delta=6.9$ (d, 1, J$=2$ Hz, 3-H), 6.1 (d,1,J$=2$ Hz, 4-H), 4.6 (s, 1, NH, exchangeable), 2.37 (s,3, CH$_3$), 1.25 (s, 9, C(CH$_3$)$_3$);

C$_9$H$_{15}$NO$_3$S (217.29)—Calc.: C-49.75%; H-6.94%; N-6.43%; S-14.71%; Found: C-49.50% H-6.97%; N-6.47%; S-15.00%.

500 ml of a 15% solution of butyl lithium (52.5 gm or 0.82 mol) in hexane were added dropwise to a solution of 81 gm (0.37 mol) of N-tert. butyl-5-methyl-furan-2-sulfonamide (cooled to $-60°$ C.) in 1 liter of anhydrous tetrahydrofuran. The reaction mixture was warmed to $-20°$ C. within 2 hours and stirred for 20 minutes at this temperature. Subsequently, the mixture was cooled to $-60°$ C. and a stream of carbon dioxide was introduced slowly. When the exothermic reaction had subsided, the mixture was heated to $-20°$ C. and carefully (evolution of CO$_2$) 136 ml of a semi-concentrated (about 18%) hydrochloric acid were added dropwise, whereby the temperature rose to 0° C. The reaction mixture was then substantially evaporated and stirred into an aqueous sodium bicarbonate solution. The aqueous solution was extracted with ether, acidified to a pH-value of 1 to 2 by means of hydrochloric acid and extracted twice with ether. The acidic ether extracts were dried and evaporated. The obtained crude product was recrystallized from benzene, yielding 81.1 gm (84% of theory) of 2-(N-tert. butyl)-sulfamoyl-5-methyl-furan-3-carboxylic acid.

M.p. 130° C.

IR (CH$_2$Cl$_2$): 1730 and 1690 cm$^{-1}$ (CO); 1H-NMR (CDCl$_3$):$\delta=6.55$ (d, 1, J$=0.5$ Hz, 4-H), 5.7 (s, 1, NH, exchangeable), 2.36 (d, 3, J$=0.5$ Hz, CH$_3$), 1.25 (s, 9, C(CH$_3$)$_3$) and 1 further exchangeable proton;

C$_{10}$H$_{15}$NO$_5$S (261.30)—Calc.: C-45.97%; H-5.79%; N-5.36% S-12.27%; Found: C-46.30%; H-5.88%; N-5.18%; S-12.20%.

Boiling stones and 42 gm (0.12 mol) of 2-(N-tert. butyl)-sulfamoyl-5-methyl-furan-3-carboxylic acid were heated in a round bottom flask for 2 hours at 150° C. The cooled reaction mixture was taken up in 1 liter of ethyl acetate. After refluxing the solution was treated with activated charcoal, filtered and evaporated. 22.8 gm (69% of theory) of crystalline 5-methyl-2-sulfamoyl-furan-3-carboxylic acid were obtained.

M.p. 191° C.

C$_6$H$_7$NO$_5$S (205.20) Calc.: C-35.12%; H-3.44%; N-6.83%; S-15.63%; Found: C-34.95%; H-3.50%; N-6.88%; S-16.00%.

EXAMPLE 2

5-Methyl-furo[3,2-d]isothiazole-3(2H)-one-1,1-dioxide-sodium salt 1.0 gm (5.3 millimols) of 5-methyl-furo[3,2-d]isothiazole-3(2H)-one-1, 1-dioxide and 230 mgm (5.3 millimols) of a 55% sodium hydride-in-oil dispersion were refluxed for 1.5 hours in 100 ml of anhydrous tetrahydrofuran. After cooling, the obtained crystals were suction-filtered off, washed with petroleum ether and dried over phosphorus pentoxide, yielding 1.05 gm (95% of theory) of 5-methyl-furo[3,2-d]isothiazole-3-(2H)-one-1,1-dioxide-sodium salt.

M.p. above 280° C. (decomp. starts at 210° C.).

C$_6$H$_4$NNaO$_4$S (209.61)—Calc.: C-34.45%; H-1.93%; N-6.70%; S-15.33%; Found: C-34.20%; H-2.08%; N-6.56%; S-15.30%.

EXAMPLE 3

5-Ethyl-furo[3,2-d]isothiazole-3(2H)-one-1,1-dioxide 5.0 gm (0.023 mol) of 5-ethyl-2-sulfamoyl-furan-3-carboxylic acid were admixed with 4.75 gm (0.023 mol of phosphorus pentachloride in 300 ml of anhydrous toluene, and the mixture was refluxed for 8 hours. After filtering, the filtrate was evaporated in vacuo and the residue was recrystallized from carbon tetrachloride, yielding 2.1 gm (46% of theory) of 5-ethyl-furo[3,2-d]isothiazole-3(2)-one-1,1-dioxide.

M.p.: 133° C.

$C_7H_7NO_4S$ (201.21)—Calc. C-41.79%; H-3.51%; N-6.96%; S-15.84%; Found: C-41.53%; H-3.35%; N-6.97%; S-15.83%.

The starting compound was prepared in the following way:

Analogous to the preparation of the 5-methyl-2-sulfamoyl-furan-3-carboxylic acid (see starting compound of Example 1), 2-ethyl furan was sulfonated with sulfur trioxide-pyridine-complex into the sodium salt of the 5-ethyl-furan-2-sulfonic acid with a yield of 32.5% of theory. After chlorinating it with phosphorus pentachloride and reacting it with tert. butyl amine, 5-ethyl-N-tert. butyl-furan-2-sulfonamide [(m.p. 71°–72° C. from petroleum ether); 1H-NMR ($CDCl_3$): $\delta=6.95$ (d, 1, J=2 Hz, 3-H), 6.15 (d, 1, J=2 Hz, 4-H), 4,7 (s, 1, NH, exchangeable), 2.73 (q, 2, $CH_2$), 1.30 (m, 12, —$CH_2$—$CH_3$ and $C(CH_3)_3$)] was obtained with a yield of 48% of theory. The two subsequent reactions were also performed in analogy to the preparation of the 5-methyl-furan compound: By metalizing with butyl lithium and by carboxylating with carbon dioxide, the 5-ethyl-2-(N-tert. butyl)-sulfamoyl-furan-3-carboxylic acid (m.p. 118°–119° C. from cyclo hexane) was obtained with a yield of 59% of theory, which was heated under dry conditions at 160° C. for 2 hours. 5-Ethyl-2-sulfamoyl-furan-3-carboxylic acid [m.p.: 186° C. (from ethyl acetate), 1H-NMR ([$d_6$]=DMSO); $\delta=6.6$ (s, 1, 4-H), 2.73 (q, 2, $CH_2$), 1.25 (t, 3, $CH_3$) and two exchangeable protons] was obtained with a yield of 87% of theory.

$C_7H_9NO_5S$ (219.22)—Cal.: C-38.35%; H-4.14%; N-6.39%; S-14.63%; Found: C-38.33% H-4.04%; N-6.70%; S-14.56%.

EXAMPLE 4

4,5-Dimethyl-furo[3,2-d]isothiazole-3(2H)-one-1,1-dioxide (a) From 4.5-Dimethyl-2-sulfamoyl-furan-3-carboxylic acid A mixture of 1.0 gm (4.6 millimols) of 4.5 -dimethyl-2-sulfamoyl-furan-3-carboxylic acid and 0.96 gm (4.6 millimols) of phosphorus pentachloride in toluene was reacted analogous to Example 1, yielding 0.68 gm (73% of theory) of 4,5-dimethyl-furo[3,2-d]isothiazole-3-(2H)-one-1,1-dioxide. $R_f$-value: 0.21 (silica gel 60 $F_{254}$ plates, thickness 0.25 mm, eluant ethylene chloride; ethyl acetate; glacial acetic acid 100:30:5).

$C_7H_7NO_4S$ (201.21)—Calc.: C-41.79%; H-3.51%; N-6.96%; S-15.94%; Found: C-41.50% H-3.56%; N-6.92%; S-15.98%.

The starting compound was prepared in the following way:

Analogous to the preparation of the 5-methyl-2-sulfamoyl-furan-3-carboxylic acid (see starting compound of Example 1), 2,3-dimethyl-furan [K. C. Rice and J. R. Dyer, J. Heterocycl. Chem. 12, 1325 (1975)] was converted with sulfur trioxide-pyridine complex into the 4,5-dimethyl-furan-2-sulfonic acid sodium salt and treated with phosphorus pentachloride and tert. butylamine. N-tert. butyl-4-,5-dimethyl-furan-3-sulfonamide was obtained with a yield of 34% of theory. M.p. 95°–96° C. (from petroleum ether).

1H-NMR ($CDCl_3$): $\delta=6.85$ (s, 1, 3-H), 4,6 (s, 1, NH, exchangeable), 2.30 (s, 3, 5-$CH_3$), 2.00 (s, 3, 4-$CH_3$), 1.26 (s, 9, $C(CH_3)_3$).

By subsequent metalizing with butyl lithium and carboxylating with carbon dioxide, 4,5-dimethyl-2-(N-tert. butyl)-sulfamoyl-furan-3-carboxylic acid was obtained with a yield of 70%.

M.p. 114°–115° C. (from petroleum ether). By dry heating in vacuo this carboxylic acid was converted into 4,5-dimethyl-2-sulfamoyl-furan-2-carboxylic acid. Yield 16% of theory.

$C_7H_9NO_5S$ (219.22)—Calc: C-38.35% H-4.14%; N-6.39%; S-14.63%; Found: C-38.40%; H-4.01%; N-6.45%; S-14.50%.

(b) From 2-(tert. butyl)-4-,5-dimethyl-furo[3,2-d]isothiazole-3(2H)-one-1,1-dioxide 0.5 gm (2.3 millimols) of 2-(tert. butyl)-4,5-dimethyl-furo[3,2-d]isothiazole-3(2H)-one-1,1-dioxide was heated in vacuo at 175° C. for 2 hours. After cooling, the reaction product was purified by column chromatography (eluant: ethylene chloride/ethyl acetate/glacial acetic acid, 100:30:5). 35 mgm (7.5% of theory) of 4,5-dimethyl-furo-3,2-d]-isothiazole-3(2H)-one-1, 1-dioxide were obtained.

$C_7H_7NO_4S$ (201.21)—Calc: C-41.79%; H-3.51%; N-6.96%; S-15.94%; Found: C-41.60%; H-3.65%; N-7.02%; S-15.85%.

The starting compound was prepared in the following way:

1.7 gm (6.2 millimols) of 4,5-dimethyl-2-(N-tert. butyl)-sulfamoyl-furan-3-carboxylic acid were admixed with 5 gm of polyphosphoric acid, and the mixture was heated for 30 minutes at 60° C. After pouring it over ice, the reaction mixture was extracted with methylene chloride, the organic phase was washed with aqueous sodium bicarbonate and with water and then evaporated. 0.65 mgm (41% of theory) of 2-(tert. butyl)-4,5-dimethyl-furo[3,2-d]isothiazole-3(2H)-one-1,1-dioxide was obtained.

$C_{11}H_{15}NO_4S$ (257.31)—Cal.: C-51.35%; H-5.88%; N-5.44%; S-12.46%; Found: C-51.20%; H-5.91%; N-5.32%; S-12.32%.

EXAMPLE 5

5-Methyl-thieno[3,2-d]isothizole-3(2)-one-1,1-dioxide (a) From 5-Methyl-2-(N-tert. butyl) sulfamoyl-thiophene-3-carboxylic acid 139 gm (0.5 mol) of 5-methyl-2-(N-tert. butyl) sulfamoyl-thiophene-3-carboxylic acid were added in portions to 500 ml of freshly prepared polyphosphoric acid cooled to 60° C. (prepared at 140° C. from 570 gm of phosphorus pentoxide and 250 ml of 85% phosphoric acid). The reaction mixture was stirred for 30 minutes at this temperature. After pouring over ice, the precipitated crude product was filtered off, washed with ice water and dried. After recrystallization from methanol 98.5 gm (97% of theory) of 5-methyl-thieno-[3,2-d]isothiazole -3(2H)-one-1,1-dioxide were obtained.

M.p.: 231° C. IR (KBr): 3200 (NH), 1740 (CO), 1325 and 1150 cm$^{-1}$ (SO$_2$), $^1$H-NMR ([d$_6$]-DMSO): δ=7.2 (d, 1, J=1 Hz, 4-H), 2,6 (d, 3, J=1 Hz, CH$_3$) and 1 exchangeable proton.

C$_6$H$_5$NO$_3$S$_2$ (203.23)—Calc.: C-35.46%; H-2.48%; N-6.89%; S-31.55%; Found: C-35.35% H-2.64%; N-7.10%; S-31.40%.

The starting compound was prepared in the following way:

291 gm (2.5 mol) of chlorosulfonic acid were added in portions to 208 gm (1.0 mol) of phosphorus pentachloride while stirring and cooling. After the evolution of hydrogen chloride had subsided, 98 gm (1.0 mol) of 2-methyl-thiophene were added dropwise while stirring at a temperature of 10° C. When the addition was finished, the mixture was stirred for another 10 minutes. After pouring the reaction mixture over 2.5 kg of ice, the obtained sulfochloride was separated by extracting 5 times with 500 ml of ether. The organic phase was washed twice with 200 ml of water, dried and evaporated in vacuo. The residual oil was taken up in 200 ml of tetrahydrofuran and added, while stirring, dropwise to a solution of 183 gm (2.5 mol) of tert. butylamine in 100 ml of tetrahydrofuran at a temperature of 20° C. The mixture was stirred for 1 hour at room temperature and for 20 minutes at 70° C. bath temperature. The crystals of tert. butylamine hydrochloride which separated out were filtered off and washed with ether. The combined filtrates were evaporated, and the residue was taken up in ether. After washing with 2 N hydrochloric acid and water, the residue was dried over sodium sulfate and again evaporated. The obtained crude product was recrystallized from cyclohexane, yielding 182 gm (78% of theory) of N-tert.-butyl-5-methyl-thiophene-2-sulfonamide.

M.p. 89° C.

117 gm (0.5 mol) of N-tert.butyl-5-methyl-thiophene-2-sulfonamide were dissolved in 1 liter of dried tetrahydrofuran and cooled to −40° C. In a nitrogen atmosphere 640 ml of a 15% solution of n-butyl-lithium in hexane (1.05 mol) were added dropwise to this solution, while keeping the temperature below −40° C. When the addition was finished, the mixture was stirred for 30 minutes at −20° C., cooled to −60° C. and a stream of carbon dioxide was passed over the reaction mixture. The strongly exothermic reaction was kept at −50° C. and when the reaction was finished, carbon dioxide passed over the mixture for another 10 minutes. The mixture was heated to −10° C., carefully acidified with concentrated hydrochloric acid (about 110 ml) and evaporated to dryness. The residue was taken up in ether (about 3 liters) and washed with water (about 2.5 liters).

After drying and evaporating of the ether phase, the crude product was recrystallized from benzene yielding 114 gm (82% of theory) of 5-methyl-2-(N-tert.butyl)-sulfamoyl-thiophene-3-carboxylic acid.

M.p. 178° C.

IR (CH$_2$Cl$_2$): 1730 and 1690 cm$^{-1}$ (CO), 1335 and 1160 (SO$_2$);

1H-NMR (CDCl$_3$+CD$_3$OD): δ=7.2 (d, 1, J=0.5 Hz, 3-H) 2.52 (d, 3, J=0.5, CH$_3$), 1.26 (s, 9, C(CH$_3$)$_3$), 2 exchangeable protons.

C$_{10}$H$_{15}$NO$_4$S$_2$ (277.37)—Calc.: C-43.30%; H-5.45%; N-5.05%; S-23.12%; Found: C-43.50%; H-5.48%; N-4.91%; S-22.82%.

(b) From 5-methyl-2-sulfamoyl-thiophene-3-carboxylic acid by reaction with polyphosphoric acid 0.5 gm (2.26 millimols) of 5-methyl-2-sulfamoyl-thiophene-3-carboxylic acid was reacted analogous to Example 5(a), yielding 0.44 gm (96% of theory) of 5-methyl-thieno[3,2-d]isothiazole-3(2H)-one-1,1-dioxide.

M.p. 231° C. (from methanol)

C$_6$H$_5$NO$_3$S$_2$ (203.23)—Calc.: C-35.46%; H-2.48%; N-6.89%; S-31.55%; Found: C-35.50%; H-2.50%; N-6.78%; S-31.48%.

The starting compound was prepared in the following way:

A mixture of 5.0 gm (18 millimols) of 2-(N-tert.butyl)-sulfamoyl-5-methyl-thiophene-3-carboxylic acid and 20 ml of o-dichloro-benzene was heated, while stirring, for 4 hours at 140° C. After cooling, the reaction mixture was taken up in a mixture of ether and the equivalent amount of dilute aqueous sodium hydroxide. After separation of the ether phase, the aqueous phase was acidified with hydrochloric acid, and the precipitated material was suction-filtered off. The filter cake was recrystallized from ethyl acetate/cyclohexane, yielding 3.3 gm (83% of theory) of 5-methyl-2-sulfamoyl-thiophene-3-carboxylic acid.

M.p.: 198° C.

C$_6$H$_7$NO$_4$S$_2$ (221.26)—Calc.: C-32.57%; H-3.19%; N-6.33%; S-28.98%; Found: C-32.89%; H-3.30%; N-6.34%; S-28.90%.

(c) From 5-methyl-2-sulfamoyl-thiophene-3-carboxylic acid by reaction with phosphorus pentachloride A mixture of 0.5 gm (2.26 millimols) of 5-methyl-2-sulfamoyl-thiophene-3-carboxylic acid, 0.5 gm (2.2 millimols) of phosphorus pentachloride and 30 ml of anhydrous toluene was refluxed for 9 hours. The mixture was worked up in analogy to Example 1 and yielded 0.41 gm (89% of theory) of 5-methyl-thieno[3,2-d]isothiazole-3-(2H)-one-1,1-dioxide.

M.p. 231° C. (from methanol).

(d) From 5-methyl-2-sulfamoyl-thiophene-3-carboxylic acid by heating in the presence of catalytic amounts of p-toluene-sulfonic acid A mixture of 0.1 gm (0.45 millimols) of 5-methyl-2-sulfamoyl-thiophene-3-carboxylic acid, 50 ml of anhydrous toluene and 5 mgm of p-toluene-sulfonic acid was heated for 10 hours in a vessel equipped with a water trap. The reaction mixture was evaporated to dryness in vacuo and separated by column chromatography. 0.40 mgm (49% of theory) of 5-methyl-thieno[3,2-d]isothiazole-3(2H)-one-1,1-dioxide were obtained.

M.p. 231° C. (from methanol).

(e) From 2-tert.butyl-5-methyl-thieno[3,2-d]isothiazole-3(2H)-one-1,1-dioxide

A mixture of 0.2 gm (0.77 millimols) of N-tert.butyl-5-methyl-thieno[3,2-d]isothiazole-3(2H)-one-1-dioxide and o-dichloro-benzene was refluxed for 8 hours. After cooling, the reaction mixture was distributed between a mixture of ether and aqueous sodium bicarbonate solution. The separated aqueous solution was acidified and extracted with methylene chloride. After evaporation and recrystallization from methanol, 0.13 gm (83% of theory) of 5-methyl-thieno[3,2-d]isothiazole-3(2H)-one-1,1-dioxide was obtained.

M.p. 231° C.

$C_6H_5NO_3S_2$ (203.23)—Calc.: C-35.46%; H-2.48%; N-6.89%; S-31.55%; Found: C-35.50%; H-2.50%; N-6.78%; S-31.48%.

The starting compound was prepared as follows:

A mixture of 3.0 gm (10.8 millimols) of 2-(N-tert.butyl)-sulfamoyl-5-methyl-thiophene-3-carboxylic acid, 2.25 gm (10.8 millimols) of phosphorus pentachloride and 60 ml of toluene was refluxed for 7 hours. The reaction mixture was filtered while hot, cooled, and 300 ml of ether were added. The mixture was washed with an aqueous sodium bicarbonate solution and water, dried and evaporated. The residue was recrystallized from cyclohexane, yielding 1.5 gm (54% of theory) of 2-tert.butyl-5-methyl-thieno[3,2-d]isothiazole-3(2H)-one-1,1-dioxide.

M.p.: 80°–81° C.

$C_{10}H_{13}NO_3S_2$ (259.35)—Calc.: C-46.31%; H-5.05%; N-5.40%; S-24.73%; Found: C-46.39%; H-5.15%; N-5.44%; S-24.45%.

(f) From methyl 5-methyl-2-sulfamoyl-thiophene-3-carboxylate 2.4 gm (10.2 millimols) of methyl 5-methyl-2-sulfamoyl-thiophene-3-carboxylate were added to a solution of 0.24 gm (10.2 millimols) of sodium in 50 ml of anhydrous methanol. After refluxing it for 4 hours the mixture was evaporated to dryness in vacuo. The residue was, as far as possible, dissolved in ethanol, and after suction filtering ether was added to the filtrate, 2.1 gm (91% of theory) of 5-methyl-thieno[3,2-d]isothiazole-3(2H)-one-1,1-dioxide sodium salt crystallized out.

M.p. 325° C. (decomp.).

$C_6H_4NNaO_3S_2$ (225.22)—Calc.: C-32.00%; H-1.79%; N-6.22%; S-28.47%; Found: C-32.00%; H-1.91%; N-6.13%; S-28.50%.

By dissolving the salt in water and acidifying the solution with hydrochloric acid the salt was converted into 5-methyl-thieno[3,2-d]isothiazole-3(2H)-one-1,1-dioxide.

M.p. 231° C.

The starting compound was prepared as follows:

A mixture of 3.0 gm (13 millimols) of 5-methyl-2-sulfamoyl-thiophene-3-carboxylic acid and 150 ml of methanolic hydrochloric acid was stirred for 2 hours at room temperature and then refluxed for 2 hours. The reaction mixture was evaporated, and the residue was dissolved in ether. After washing with diluted aqueous sodium bicarbonate and with water, drying, evaporating in vacuo and recrystallization from methanol/water, 2.9 gm (95% of theory) of methyl 5-methyl-2-sulfamoyl-thiophene-3-carboxylate were obtained.

M.p.: 137°–138° C.

$C_7H_9NO_4S_2$ (235.29)—Calc.: C-35.73%; H-3.86%; N-5.95%; S-27.25%; Found: C-36.20%; H-4.00%; N-5.95%; S-27.50%.

EXAMPLE 6

Salts of 5-methyl-thieno[3,2-d]isothiazole-3(2H)-one-1,1-dioxide (a)

5-Methyl-thieno[3,2-d]isothiazole-3(2H)-one-1,1-dioxide sodium salt

A solution of 4.0 gm (0.1 mol) of sodium hydroxide in 50 ml of water was added to a solution of 20.3 gm (0.1 mol) of 5-methyl-thieno[3,2-d]isothiazole-3(2H)-one-1,1-dioxide in 500 ml of ethanol. The mixture was evaporated to dryness and the residue was recrystallized from ethanol/ether. 17.5 gm (78% of theory) of 5-methyl-thieno[3,2-d]isothiazole-3(2H)-one-1,1-dioxide sodium salt were obtained.

M.p. 325° C. (decomp.).

IR (KBr): 1630 cm$^{-1}$ (CO).

$C_6H_4NNaO_3S_2$ (225.22)—Calc.: C-32.00%; H-1.79%; N-6.22%; S-28.47%; Found: C-32.20%; H-1.88%; N-6.01%; S-28.15%.

(b)

5-Methyl-thieno[3,2-d]isothiazole-3(2H)-one-1,1-dioxide calcium salt 500 ml of methanol were added to 0.49 gm (12.3 millimols) of calcium, the mixture was refluxed, and 5.0 gm (24.6 millimols) of 5-methyl-thieno[3,2-d]isothiazole-3(2H)-one-1,1-dioxide were added to the suspension thus obtained. The resulting solution was evaporated, and the residue was recrystallized from a little ethanol/ether. 3.9 gm (71% of theory) of 5-methyl-thieno[3,2-d]-isothiazole-3(2H)-one-1,1-dioxide calcium salt were obtained.

M.p. 306°–308° C. (decomp.).

$C_{12}H_8CaN_2O_6S_4$ (444.55)—Calc.: C-32.42%; H-1.81%; N-6.31%; S-28.85%; Found: C-32.55%; H-2.05%; N-6.12%; S-28.88%.

(c)

5-Methyl-thieno[3,2-d]isothiazole-3(2H)-one-1,1-dioxide ammonium salt

Prepared analogous to Example 2(a) from 5-methyl-thieno-[3,2-d]isothiazole-3(2H)-one-1,1-dioxide and aqueous ammonia with a yield of 81% of theory.

M.p. 224° C. (from ethanol/ether).

$C_6H_8N_2O_3S_2$ (220.28)—Calc.: C-32.72%; H-3.66%; N-12.72%; S-29.11%; Found: C-32.90%; H-3.46%; N-12.62%; S-29.20%.

(d)

5-Methyl-thieno[3,2-d]isothiazole-3(2H)-one-1,1-dioxide potassium salt

Prepared analogous to Example 2(a) from 5-methyl-thieno[3,2-d]isothiazole-3(2H)-one-1,1-dioxide and aqueous potassium hydroxide with a yield of 84% of theory.

M.p.: 297° C. (from ethanol/ether).

$C_6H_4KNO_3S_2$ (241.34)—Calc.: C-29.86%; H-1.67%; N-5.80%; S-26.57%; Found: C-29.81%; H-1.74%; N-5.94%; S-26.35%.

EXAMPLE 7

5-Ethyl-thieno[3,2-d]isothiazole-3(2H)-one-1,1-dioxide 42.0 gm (0.144 mol) of 5-ethyl-2(N-tert.butyl)-sulfamoyl-thiophene-3-carboxylic acid were added to 150 ml of polyphosphoric acid, and the mixture was heated at 80° C. for 20 minutes. The reaction mixture was poured over ice, and the precipitated crude product was filtered off, washed with ice and dried. After recrystallization from benzene and from ethyl acetate, 15.9 gm (51% of theory) of 5-ethyl-thieno[3,2-d]isothiazole-3(2H)-one-1,1-dioxide were obtained.

M.p. 143° C.

IR (CH$_2$Cl$_2$): 3350 (NH), 1740 (CO), 1340 and 1150 cm$^{-1}$ (SO$_2$);

$C_7H_7NO_3S_2$ (217.27)—Calc.: C-38.70%; H-3.25%; N-6.45%; S-29.52%; Found: C-38.50%; H-3.24%; N-6.33%; S-29.80%.

The starting compound was prepared in the following way:

222 gm (1.07 mol) of phosphorus pentachloride were added in portions while stirring and cooling to 310 gm (2.7 mol) of chlorosulfonic acid. After the evolution of hydrogen chloride had subsided, 100 gm (0.89 mol) of 2-ethyl-thiophene were added dropwise while stirring at a temperature of 20° C. When the addition was finished, the reaction mixture was poured over ice and extracted with ether. The ether solution was washed until neutral, dried and evaporated. The residue was taken up in tetrahydrofuran, and the solution was added dropwise to a solution of 169 gm (2.3 mol) of tert.butylamine in 200 ml of tetrahydrofuran. After refluxing for 3 hours, the reaction mixture was filtered to separate the precipitated tert.butylamine hydrochloride, and the filtrate was evaporated in vacuo. The residue was taken up in ether and the solution was washed with dilute hydrochloric acid and with water, dried and evaporated. 147 gm of crude product were obtained which, after purification on a silica gel column (4 kg of silica gel 40 for column chromatography, particle size 0.2–0.5 mm; eluant: cyclohexane/ethyl acetate 4:1), yielded 117.6 gm (53% of theory) of 5-ethyl-N-tert.butyl-thiophene-2-sulfonamide.

M.p. 38° C.

$C_{10}H_{17}NO_2S_2$ (247.39)—Calc.: C-48.55%; H-6.93%; N-5.66%; S-25.92%; Found: C-48.20%; H-6.86%; N-5.72%; S-25.60%.

56.8 gm (0.23 mol) of 5-ethyl-N-tert.butyl-thiophene-2-sulfonamide were dissolved in 500 ml of dried tetrahydrofuran, and the solution was cooled to −20° C. 310 ml of a 15% solution of n-butyl-lithium (0.5 mol) in hexane were added dropwise at this temperature. After stirring for 2 hours, the reaction mixture was poured over solid carbon dioxide (dry ice), evaporated and distributed between water and ether. The aqueous phase was acidified and extracted with ether. The ether extract was evaporated, and the residue was recrystallized from cyclohexane/petroleum ether. 42 gm (63% of theory) of 5-ethyl-2-(N-tert.butyl)-sulfamoyl-thiophene-3-carboxylic acid were obtained.

M.p. 135° C.

$C_{11}H_{17}NO_4S_2$ (291.40)—Calc.: C-45.34%; H-5.88%; N-4.81%; S-22.01%; Found: C-45.40%; H-5.91%; N-4.90%; S-22.00%.

EXAMPLE 8

5-Ethyl-thieno[3,2-d]isothiazole-3(2H)-one-1,1-dioxide sodium salt 10.5 gm (48 millimols) of 5-ethyl-thieno[3,2-d]isothiazole-3(2H)-one-1,1-dioxide were dissolved in ethanol. The solution was adjusted to pH 7 with aqueous sodium hydroxide. After evaporating the solution in vacuo and recrystallizing the residue from tetrahydrofuran, 6.6 gm (57.5% of theory) of 5-ethyl-thieno[3,2-d]isothiazole-3(2H)-one-1,1-dioxide sodium salt were obtained.

M.P. 273°–275° C. (decomp.).

$C_7H_6NNaO_3S_2$ (239.26)—Calc.: C-35.41%; H-2.53%; N-5.86%; S-26.80%; Found: C-34.90%; H-2.67%; N-5.69%; S-26.70%.

EXAMPLE 9

4,5-Dimethyl-thieno[3,2-d]isothiazole-3(2H)-one-1,1-dioxide 20.0 gm (68.6 millimols) of 2-(N-tert.butyl) sulfamoyl-4,5-dimethyl-thiophene-3-carboxylic acid were added to 100 ml of polyphosphoric acid, and the mixture was heated at 80° C. for 1 hour. Subsequently, the reaction mixture was poured over ice, and the raw product which crystallized out (14 gm) was filtered off, dried and recrystallized twice from benzene. 12.5 gm (84% of theory) of 4.5-dimethyl-thieno[3,2-d]isothiazole-3(2H)-one-1,1-dioxide were obtained.

M.p. 187° C.

IR ($CH_2Cl_2$): 3350 (NH), 1730/1720 (CO), 1340 and 1175 cm$^{-1}$ ($SO_2$).

1H-N MR ($CDCl_3$): $\delta = 7.5$ (1, NH, exchangeable), 2,5 (3, s, 5-$CH_3$), 2.35 (3, s, 4-$CH_3$).

$C_7H_8NO_3S_2$ (217.27)—Calc.: C-38.70%; H-3.25%; N-6.45%; S-29.52%; Found: C-38.50%; H-3.21%; N-6.39%; S-29.35%.

The starting compound was prepared as follows: 22.0 gm (0.196 mol) of 2,3-dimethyl-thiophene were converted into 25.0 gm of N-tert.butyl-4,5-dimethyl-thiophene-2-sulfonamide in analogy to the conversion of 2-ethyl-thiophene (see starting compound of Example 7) with chlorosulfonic acid/phosphorus pentachloride via 4,5-dimethyl-thiophene-2-sulfonic acid chloride and then with tert.butylamine. Yield: 51.5% of theory.

M.p. 102° C. (from petroleum ether).

1H-NMR ($CDCl_3$): $\delta = 7.35$ (s, 1,3-H), 4.8 (s, 1, NH, exchangeable), 2.45 (s, 3, 5-$CH_3$), 2.2 (s, 3, 4-$CH_3$), 1.35 (s, 9, C($CH_3$)$_3$);

$C_{10}H_{17}NO_2S_2$ (247.39)—Calc.: C-48.55%; H-6.93%; N-5.66%; S-25.92%; Found: C-48.40%; H-6.97%; N-5.66%; S-25.70%.

The subsequent reactions with n-butyl-lithium in tetrahydrofuran at temperatures between −60° C. to −20° C. and with carbon dioxide, also at −60° C. to −20° C., produced a yield of 26.3 gm (90% of theory) of 2-(N-tert.butyl) sulfamoyl-4,5-dimethyl-thiophene-3-carboxylic acid.

M.p. 193°–194° C. (from benzene).

IR (KBr); 3230 (NH and OH), 1725 and 1710 (CO), 1310 and 1130 cm$^{-1}$ ($SO_2$);

1H-NMR ($CDCl_3 + CD_3OH$): $\delta = 2.4$ (s, 3, 5-$CH_3$), 2.28 (s, 3, 4-$CH_3$), 1.3 (s, 9, C($CH_3$)$_3$) and 2 exchangeable protons.

EXAMPLE 10

Salts of 4,5-dimethyl-thieno[3,2-d]isothiazole-3(2H)-one-1,1-dioxide (a)

4,5-Dimethyl-thieno[3,2-d]isothiazole-3(2H)-one-1,1-dioxide sodium salt 3.0 gm (13.8 millimols) of 4,5-dimethyl-thieno[3,2-d]isothiazole-3(2H)-one-1,1-dioxide were dissolved in an aqueous solution of 1.16 gm (13.8 millimols) of sodium bicarbonate in 50 ml of water. The resulting solution was evaporated in vacuo, and the residue was recrystallized from ethanol. 2.5 gm (76% of theory) of 4,5-dimethyl-thieno[3,2-d]isothiazole-3(2H)-one-1,1-dioxide sodium salt were obtained.

M.p. above 250° C. (decomp.)

$C_7H_6NNaO_3S_2$ (239.26)—Calc.: C-35.14%; H-2.59%; N-5.85%; S-26.80%; Found: C-35.40%; H-2.70%; N-5.88%; S-26.90%.

(b)
4,5-Dimethyl-thieno[3,2-d]isothiazole-3(2H)-one-1,1-dioxide calcium salt 37 mgm (0.5 millimols) of calcium hydroxide and 217 mgm (1 millimol) of 4,5-dimethyl-thieno[3,2-d]isothiazole-3-(2H)-one-1,1-dioxide were added to 50 ml of boiling water. The virtually clear resulting solution was filtered and evaporated to 1 ml. 180 mg (76% of theory) of 4,5-dimethyl-thieno[3,2-d]-isothiazole-3(2H)-one-1,1-dioxide calcium salt crystallized out.

M.p. >320° C. (decomp.)

$C_{14}H_{12}N_2O_6S_4Ca$ (472.61)—Calc.: C-35.58%; H-2.56%; N-5.93%; S-27.14%; Found: C-35.30%; H-2.71%; N-5.74%; S-26.84%.

EXAMPLE 11

4-Ethyl-5-methyl-thieno[3,2-d]isothiazole-3(2H)-one-1,1-dioxide

A mixture of 3.05 gm (10 millimols) of 4-ethyl-5-methyl-2-(N-tert.butyl)-sulfamoyl-thiophene-4-carboxylic acid and 20 ml of polyphophoric acid was heated at 65° C. for 30 minutes. Subsequently, the reaction mixture was poured over ice, and the resulting crystalline precipitate was filtered off, washed with ice water and dried. 2.1 gm (91% of theory) of 4-ethyl-5-methyl-thieno[3,2-d]isothiazole-3(2H)-one-1,1-dioxide were obtained.

$R_f$-value: 0.19 (TLC-prefabricated plates, silica gel 60 $F_{254}$, thickness of the layer 0.25 mm; eluant:ethylene chloride/ethyl acetate/glacial acetic acid 100:30:5).

$C_8H_9NO_3S_2$ (231.29)—Calc.: C-41.54%; H-3.92%; N-6.06%; S-27.73%; Found: C-41.35%; H-3.90%; N-6.14%; S-27.62%.

The starting compound was prepared as follows:

3-ethyl-2-methyl-thiophene [W. Steinkopf, A. Merckoll and H. Straunch, Liebigs Ann. Chem. 545,45 (1940)] was reacted, analogous to 2-methyl-thiophene (see Example 5) with phosphorus pentachloride and chlorosulfonic acid, and the resulting sulfochloride was treated with tert.butylamine. By metalizing with n-butyl-lithium and carboxylating with carbon dioxide, also in analogy to the preparation of 5-methyl-2-(N-tert.butyl) sulfamoyl-thiophene-3-carboxylic acid, 4-ethyl-5-methyl-2-(N-tert.butyl) sulfamoyl-thiophene-3-carboxylic acid was obtained. $R_f$-value: 0.27 (TLC-prefabricated plates, silica gel 60 $F_{254}$, thickness of the layer 0.25 mm, eluant:ethylene chloride/ethyl acetate/glacial acetic acid 100:30:5);

$C_{12}H_{19}NO_4S_2$ (305.42)—Calc.: C-47.19%; H-6.27%; N-4.59%; S-21.00%; Found: C-46.95%; H-6.31%; N-4.52%; S-20.92%.

As indicated above, the compounds of the present invention, that is, those embraced by formula I and their non-toxic salts, are useful as sweetening agents.

Our discovery that the compounds of the present invention are very powerful sweetening agents is unobvious and surprising inasmuch as 5-methyl-saccharin, which comprises a —CH=CH-group in place of the heteroatom—X— in formula I, and its alkali metal salts possess no sweetening power comparable to saccharin, although it is well known that a —CH=CH— group is virtually equivalent in its effect on the ring system to an —S— group, for example. It had to be assumed, therefore, that the compounds of this invention would be considerably inferior with respect to their sweetening power to thieno[3,2-d]isothiazole-3(2H)-one-1,1-dioxide.

The condensed isothiazole-3(2H)-one-1,1-dioxides of the formula I above are, from the chemical viewpoint, closely related to the thieno isothiazolone dioxides disclosed in German Offenlegungsschrift No. 2,534,689, but they are distinguishable over the prior art compounds because of the following advantageous properties:

(a) The alkyl substituent $R_2$ in the molecule of the dioxides of the present invention significantly contributes toward an improvement in taste; for instance, they do not have the unpleasant after-taste associated with saccharin. Moreover, the presence of the alkyl group in the 5-position provides a different metabolization route, wherefore the novel compounds exhibit a different toxicologic and metabolic behavior.

(b) The dioxides of the instant invention are considerably more readily accessible, because the α-positioned alkyl group in the thiophene or furan starting compound makes it easy to introduce a sulfo group in the α'-position and a carboxyl group in the β'-position with high yields and great purity of the end product.

(c) The sweetening power is stronger.

The compounds of the present invention were tested for sweetening power in comparison to certain prior art compounds, as well as for pharmacological effects, toxicity and mutagenic effects, as described below, and the results of these tests for a few representative species were as follows, where A = 5-Methyl-furo[3,2-d]isothiazole-3-(2H)-one-1,1-dioxide,
B = 5-Methyl-thieno[3,2-d]isothiazole-3(2H)-one-1,1-dioxide,
C = 5-Methyl-thieno[3,2-d]isothiazole-3-(2H)-one-1,1-dioxide sodium salt,
D = 5-Methyl-thieno[3,2-d]isothiazole-3(2H)-one-1,1-dioxide calcium salt,
E = 4,5-Dimethyl-thieno[3,2-d]isothiazole-3(2H)-one-1,1-dioxide,
F = 4,5-Dimethyl-thieno[3,2-d]isothiazole-3(2H)-one-1,1-dioxide sodium salt,
U—Cyclamate,
V = Saccharin,
W = Saccharin sodium and
X = Thieno[3,2-d]isothiazole-3(2H)-one-1,1-dioxide.

(a) Determination of the threshold concentration

From novel compounds A, B, C, D, E and F and from known comparison compounds U, V and W aqueous solutions in concentrations of 1:12500, 1:25000, 1:50000, 1:100000 and 1:200000 were prepared and evaluated by each of 5 taste testers according to the following criteria: Very sweet (=3 points); medium sweet (=2 points), slightly sweet (=1 point) and not sweet (=0 point). The tests were carried out according to the method of H. G. Schutz and F. J. Pilgrim [Food Research 22, 206 (1957)]. The dilution with perceptible sweetness was defined as the concentration at which the average value reached the evaluation points 1.0 or higher.

The following table shows the results obtained:

| Compound | Concentration | Average Value of Evaluation Points | Dilution with Perceptible Sweetness |
|---|---|---|---|
| Invention: | | | |

-continued

| Compound | Concentration | Average Value of Evaluation Points | Dilution with Perceptible Sweetness |
|---|---|---|---|
| A | 1:12500 | 1.4 | 1:12500 |
|   | 1:25000 | 0.2 |  |
| B | 1:25000 | 2.2 | 1:50000 |
|   | 1:50000 | 1.4 |  |
|   | 1:100000 | 0.2 |  |
| C | 1:25000 | 2.0 | 1:50000 |
|   | 1:50000 | 1.2 |  |
|   | 1:100000 | 0.2 |  |
| D | 1:25000 | 1.8 | 1:50000 |
|   | 1:50000 | 1.0 |  |
|   | 1:100000 | 0.0 |  |
| E | 1:50000 | 2.2 | 1:100000 |
|   | 1:100000 | 1.6 |  |
|   | 1:200000 | 0.4 |  |
| F | 1:50000 | 2.0 | 1:100000 |
|   | 1:100000 | 1.4 |  |
|   | 1:200000 | 0.2 |  |
| Prior Art |  |  |  |
| U | 1:12500 | 0.4 | >1:12500 |
| V | 1:25000 | 2.4 | 1:50000 |
|   | 1:50000 | 1.2 |  |
|   | 1:100000 | 0.4 |  |
| W | 1:25000 | 2.2 | 1:50000 |
|   | 1:50000 | 1.2 |  |
|   | 1:100000 | 0.0 |  |

(b) Determination of the relative sweetening power in comparison to saccharose

The relative sweetening power (often also defined as degree of sweetness) of sweetening agents in comparison to saccharose (cane sugar) varies with the concentrations within wide limits. Thus, in the usual concentrations (corresponding to a 2–10% solution of saccharose) the relative sweetening power of saccharin varies from 200 to 700. Therefore, for the determination of the relative sweetening power of the above-mentioned compounds a 3% aqueous solution of saccharose was always used for comparison.

The further determination of the relative sweetening power was continued according to the methods of R. Pauli [Chemiker-Zeitung 44, 744 (1920)] and T. Paul [Chemiker-Zeitung 45, 38 (1921)]. Each test series was tested by 4 taste testers.

The obtained results are given in the following table:

| Compound | Relative Sweetening Power (Saccharose = 1) |
|---|---|
| Invention: |  |
| A | 150 |
| B | 550 |
| C | 550 |
| D | 500 |
| E | 1050 |
| F | 1000 |
| Prior Art |  |
| U | 60 |
| V | 550 |
| W | 550 |
| X | 350+ |

+ This value is given on page 6 of the German Offenlegungsschrift 2,534,689).

(c) Evaluation of taste quality

The sweetening agents heretofore known, especially saccharin, do not have the taste quality of saccharose. They often have a side-taste or after-taste. Novel compounds A to F are, however, characterized by a very pure sweet taste. The compounds A and C achieve the taste quality of saccharose (cane sugar).

The compounds of the formula I were further tested with regard to possible pharmacological effects and with regard to their acute toxicity and their possible mutagenic effects.

(d) Examination of pharmacological effects

Compound C was tested by the following pharmacological tests:

The substance shows no muscle-relaxing and coordination inhibitory effects in mice; even at dosages of 200 mgm/kg p.o. the mice were able to hold themselves in rotating cylinders. At the same dosage the motility of mice was tested in light beam cages; here it could also be determined that compound C does not influence the spontaneous motility of mice.

Also, the test of the motility of rats in electric activity cages according to Führer and Feldhofer [Arzneim. Forsch. 11, 1027, (1961)] did not show any effect on the spontaneous motility of the rats. Moreover, no effect regarding the body temperatures of the rats at a dosage of 200 mg/kg p.o. could be observed. The measurements were made after 1, 2, 3 and 4 hours after oral administration of the substance; one control group only received the distilled water solvent.

Compound C has no effect on the hexobarbital narcosis in mice. At a dose of 25 mgm/kg p.o. the duration of the loss of the righting reflex was tested; the duration of the narcosis was not influenced.

At dosages of 200 mgm/kg p.o. the stimulation of the root of the tail by means of a tail clamp according to Haffner on mice did not show any influence on the defensive reactions to the pain stimuli.

Compound C also does not influence the electroshock convulsion in mice (dosage 200 mgm/kg p.o.). It also has no influence on the hypothermia of male mice, which is caused by reserpine. Compound C does not cause any ulcerations in the intestinal tract of the rat when 3 times 200 mgm/kg p.o. of the substance are administered. The test regarding the local compatibility in the eye of the rabbit showed the following result: a 1% solution causes no mydriasis, no redness of the conjunctiva and no local anesthesia.

The compound C had no effect on the contractility and the frequency of the isolated, beating atrium of the rat heart. When compound C was given in doses of 1.0 and 3.0 and 10.0 mg/kg i.v. no effect on blood pressure, heart rate and respiration of anesthetized cats could be observed. At concentrations of $1 \times 10^{-4}$ mol/liter compound C had no effect on the ADP-induced, thrombine-induced and collagen-induced aggregation of the thrombozytes in the platelet-rich plasma of healthy test persons. The measurement of the secretion of $Na^+$, $K^+$, $Cl^-$ and liquid in water-loaded male rats showed no effect by compound C (dosage 200 mgm/kg p.o.) Compound C is neither bacteriostatically nor fungistatically effective.

(e) Orienting acute toxicity

The acute toxicity was determined after oral administration to male and female mice and to male and female rats. The substances were given in an aqueous solution or as a suspension in tylose. The following table shows the animals which died within 1 to 7 days after administration of the doses indicated:

| Compound | Dose mgm/kg | Kind of animal | Number of animals | Animals which died within the observ. time of 1 day | Animals which died within the observ. time of 7 days |
|---|---|---|---|---|---|
| A | 1000 | mouse | 6 | 0 | 0 |
| B | 5000 | mouse | 6 | 0 | 0 |
| C | 5000 | rat | 6 | 0 | 0 |
| D | 5000 | mouse | 6 | 0 | 0 |
| E | 1000 | mouse | 6 | 0 | 0 |

During the observation time no toxic symptoms could be observed in the animals. All animals survived and showed a completely normal behavior.

(f) Test for mutagenic effects

The most important requirement of sweetening agents is that these substances must be harmless and safe. Most of the sweetening agents however, do not meet with this requirement. Thus, for example, saccharin shows a mutagenic effect [R. P. Batzinger, S.-Y. L. On and E. Bueding, Science 198, 944 (1977)], which casts a doubt on its use as a sweetening agent.

Compounds C and D were tested in the AMES-system [Mutation Research 31, 347–364 (1975)] with regard to their mutagenic properties. In order to show the whole spectrum of induced molecular DNA-damages (base substitutions, frame-shift mutations, deletions) the auxotrophic bacterial strains *Salmonella typhimurium* TA 98, TA 100 and *Escherichia coli* WP 2 (P) were used as genetic indicators. The strains *Salmonella typhimurium* Ta 1535, TA 1537 and TA 1538 were additionally used in the test of compound C.

The tests for all microorganisms were carried out in a way such that the influence of a microsomal enzyme system, together with the corresponding co-factors, could be tested with regard to the test substance, and to determine the differences in enzyme induction. The tests were performed without an activating system and in the presence of an activating system. For the in vitro-activation, S-9 supernatants (fraction of the endoplasmatic reticulum) of normal, i.e. not pre-treated rats and of Aroclor 1254 (500 mg/kg) induced rats were used. From the S-9 induced fraction, 3 different concentration levels were tested.

The substance concentrations of compound C were 0.1 and 0.5 mgm/plate and the concentrations of compound D were 5, 10, 15 and 20 mg/plate. In a previous series dilution essay, the highest dosages still did not show any inhibition of the microorganism growth.

Compounds C and D did not lead to an increase in the spontaneous mutation rate in any of the tested strains. An effect of the enzyme induction and of the activating fraction on the reverse mutation rate was not detectable. The colonies counted on the substance plates were within the spontaneous range of each of the test strains.

The experiments showed that compounds C and D do not release base substitutions (S. typhimurium TA 1535, TA 100, E. coli WP2 (P) and frame-shift mutations (S. typhimurium TA 1537, TA 1538, TA 98), and therefore do not indicate a mutagenic potential for compounds C and D.

For use as sweetening agents for foods and beverages the compounds of the present invention are incorporated into conventional sugar-substitute compositions, such as tablets, powders or solutions, in amounts sufficient to provide the desired sweetening power.

The following examples illustrate a few such sweetening compositions containing a compound of the instant invention as a sweetening ingredient and represent the best modes contemplated of using the invention.

The parts are parts by weight unless otherwise specified.

EXAMPLE 12

Solution

The solution is compounded from the following ingredients:

| | |
|---|---|
| Sodium salt of 5-methyl-thieno-[3,2-d]isothiazole-3(2H)-one-1,1-dioxide | 2.0 parts |
| Sorbic acid | 0.1 parts |
| Citric acid | 1.2 parts |
| Disodium phosphate | 1.5 parts |
| Distilled water | 100.0 parts by vol. |

Preparation

The sweetening ingredient, the sorbic acid, the citric acid and the disodium phosphate are successively dissolved in the distilled water at 60° C. while stirring. 1 ml (corresponding to about 20 drops) of the solution contains 20 mgm of the sweetening ingredient and is equal in sweetening power to about 2 lumps of sugar.

EXAMPLE 13

Tablets

The tablet composition is compounded from the following ingredients:

| | |
|---|---|
| 4,5-Dimethyl-thieno[3,2-d]isothiazole-3(2H)-one-1,1-dioxide | 5.0 parts |
| Sodium bicarbonate | 2.5 parts |
| Sorbitol, powdered | 42.5 parts |
| Total | 50.0 parts |

Preparation

The sweetening ingredient is intimately admixed with the sodium bicarbonate and the sorbitol, and the mixture is compressed at no more than 60% relative humidity into 50 mgm-tablets. Each tablet contains 5 mgm of the sweetening ingredient and is equivalent in sweetening power to about one lump of sugar.

Any one of the other compounds embraced by formula I or a non-toxic salt thereof may be substituted for the particular sweetening ingredient in Examples 12 and 13. Likewise, the amount of sweetening ingredient in these illustrative examples may be varied to achieve the desired sweetening power, and the amounts and nature of the inert carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. 4,5-Dimethyl-thieno[3,2-d]isothiazole-3(2H)-one-1,1-dioxide or a non-toxic salt thereof formed with an inorganic or organic base.

2. A sweetening composition for foods and beverages consisting essentially of an inert carrier and an effective sweetening amount of a compound of claim 1.

3. The method of sweetening foods and beverages which composes adding thereto an effective sweetening amount of a compound of claim 1.

* * * * *

UNITED STATES PATENT AND TRADEMARK OFFICE
CERTIFICATE OF CORRECTION

PATENT NO. : 4,233,333
DATED : November 11, 1980
INVENTOR(S) : GÜNTER TRUMMLITZ ET AL.

It is certified that error appears in the above—identified patent and that said Letters Patent is hereby corrected as shown below:

Column 5, line 11: "3(2)-one" should read -- 3(2H)-one --.

line 28: "-CH-" should read -- $-CH_2-$ --.

line 29: Cancel " $_2-$ ".

Column 6, line 31: "furo-3,2-d]" should read -- furo-[3,2-d] --.

Column 11, line 60: "C-35.41%" should read -- C-35.14% --.

Signed and Sealed this

Tenth Day of February 1981

[SEAL]

Attest:

RENE D. TEGTMEYER

Attesting Officer      Acting Commissioner of Patents and Trademarks